US012702399B2

(12) United States Patent
Veezhinathan

(10) Patent No.: US 12,702,399 B2
(45) Date of Patent: Aug. 11, 2026

(54) HANDHELD SELF-PUNCHING DEVICE

(71) Applicant: Biomet Manufacturing, LLC, Warsaw, IN (US)

(72) Inventor: Jai Abhishekh Veezhinathan, Warsaw, IN (US)

(73) Assignee: Biomet Manufacturing, LLC, Warsaw, IN (US)

(*) Notice: Subject to any disclaimer, the term of this patent is extended or adjusted under 35 U.S.C. 154(b) by 126 days.

(21) Appl. No.: 18/436,893

(22) Filed: Feb. 8, 2024

(65) Prior Publication Data

US 2024/0268811 A1 Aug. 15, 2024

Related U.S. Application Data

(60) Provisional application No. 63/444,411, filed on Feb. 9, 2023.

(51) Int. Cl.
*A61B 17/04* (2006.01)
*A61B 17/00* (2006.01)

(52) U.S. Cl.
CPC ............................... *A61B 17/0401* (2013.01); *A61B 2017/00398* (2013.01); *A61B 2017/00548* (2013.01); *A61B 2017/0409* (2013.01); *A61B 2017/0464* (2013.01)

(58) Field of Classification Search
None
See application file for complete search history.

(56) References Cited

U.S. PATENT DOCUMENTS 4,332,254 A * 6/1982 Lundquist ........... A61M 25/104 604/920
5,520,700 A * 5/1996 Beyar ................ A61B 17/0482 606/232
5,562,691 A * 10/1996 Tano ................... A61F 9/00763 606/166
5,782,843 A * 7/1998 Aasberg .................... A61F 2/10 606/187
6,193,732 B1 * 2/2001 Frantzen .............. A61B 17/128 606/151
10,405,849 B1 * 9/2019 Cole .................. A61B 17/0401
2005/0203552 A1 * 9/2005 Laufer ................... A61B 17/10 606/157
2006/0161185 A1 * 7/2006 Saadat ............... A61B 17/0487 606/153

(Continued)

*Primary Examiner* — Shaun L David
(74) *Attorney, Agent, or Firm* — SCHWEGMAN LUNDBERG & WOESSNER, P.A.

(57) ABSTRACT

A device can include a housing, an actuator, a power source, a converter, and a soft tissue anchor receiver. The actuator can extend from outside the housing to inside the housing, can be engageable by a user to implant the soft tissue anchor, and can be operable between an open position and a closed position. The power source can be removably inserted at least partially within the housing, can be configured to store energy, and can be controlled by the actuator. The converter can be located within the housing, selectively connected to the power source via the actuator such that in the open position, the actuator can connect the converter to the power source to energize the converter, and operable to extend a rod outside of the housing. The soft tissue anchor receiver can be attached to the rod and configured to hold the soft tissue anchor.

15 Claims, 3 Drawing Sheets

(56) References Cited

U.S. PATENT DOCUMENTS

2007/0088390 A1* 4/2007 Paz .................... A61B 17/0401 606/232
2007/0173706 A1* 7/2007 Neinast ................ A61B 5/6849 600/309
2008/0027472 A1* 1/2008 Nielsen ................ A61B 17/072 606/153
2008/0255592 A1* 10/2008 Hsu ....................... A61F 5/0086 606/149
2010/0121355 A1* 5/2010 Gittings ............. A61B 17/0642 606/232
2010/0286791 A1* 11/2010 Goldsmith ....... A61B 17/12022 604/524
2010/0292710 A1* 11/2010 Daniel ............... A61B 17/0401 606/142
2010/0292731 A1* 11/2010 Gittings ............. A61B 17/0401 606/232
2014/0025125 A1* 1/2014 Sack .................. A61B 17/8625 606/232
2015/0150617 A1* 6/2015 Giordano ......... A61B 17/06128 606/329
2016/0074088 A1* 3/2016 Mirza .................. A61B 17/921 606/232
2017/0156732 A1* 6/2017 Lehrberg ............... A61B 90/96
2017/0189081 A1* 7/2017 Dauster .............. A61B 17/7086
2018/0125475 A1* 5/2018 Lozier ................ A61B 17/0483
2019/0059985 A1* 2/2019 Shelton, IV ..... A61B 17/07207
2020/0100781 A1* 4/2020 Brunsvold ......... A61B 17/0401
2020/0297489 A1* 9/2020 Bishop .................. A61F 2/2466
2024/0206868 A1* 6/2024 Sauer, Md ......... A61B 17/0625

* cited by examiner

HANDHELD SELF-PUNCHING DEVICE

CLAIM OF PRIORITY

This application claims the benefit of U.S. Provisional Patent Application Ser. No. 63/444,411, filed on Feb. 9, 2023, the benefit of priority of which is claimed hereby, and which is incorporated by reference herein in its entirety.

TECHNICAL FIELD

Embodiments described herein generally relate to a handheld medical device. More specifically, embodiments described herein generally relate to a handheld self-punching device.

BACKGROUND

Soft tissue suture anchors are typically manually installed within a bone of a patient. For example, a surgeon can use a suture anchor to secure the soft tissue to the bone. Generally, surgeons will use a guide to pre-drill a hole into the bone of the patient, insert a suture anchor through the guide, and tap or hammer the suture anchor to implant the suture anchor within the bone of the patient. The inventor of the present application has produced a handheld self-punching device that can insert a soft suture anchor into the bone of the patient.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

The present disclosure relates to a push-button actuated medical device that is configured to insert an anchor for a suture into a portion, e.g., a cortico-cancellous region, any other portion or region of a bone, e.g., tibia, fibula, humerus, femur, any other bone, or the like, of a patient. The inventor of the present disclosure has developed the present device to simplify the process and decrease an amount of time that it takes to implant an anchor for a suture into the bone of the patient. Moreover, the device of the present disclosure can result in a more predictable anchor installation that can result in more consistent recovery timelines for the patient.

The above discussion provides an overview of subject matter of the present patent application. It is not intended to provide an exclusive or exhaustive explanation of the invention. The description below provides further information about the present patent application.

Figure 1:
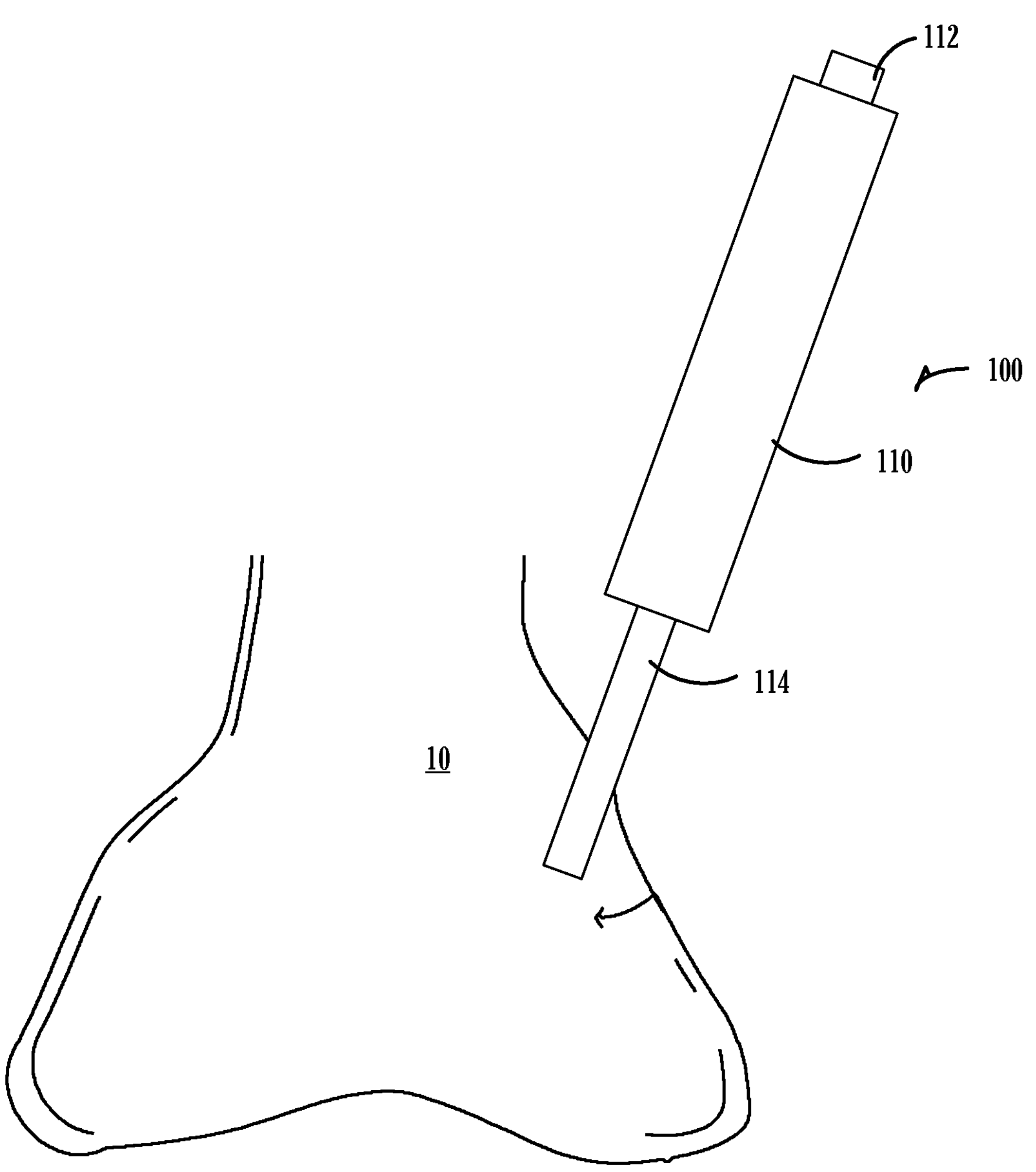
FIG. 1 is a schematic diagram of an example of a handheld self-punching device inserting an anchor and a suture into a bone of a patient, according to an embodiment.

FIG. 1 is a schematic diagram of an example of a handheld self-punching device, e.g., a device 100, for inserting an anchor for a suture into a bone, e.g., a bone 10 of a patient, according to an embodiment. The device 100 can include a housing 110, a push button or an actuator 112, and a soft tissue anchor receiver 114.

The bone 10 can be any bone of a patient. For example, the bone 10 can be a humerus, femur, tibia, fibula, or the like. The bone 10 can be a bone adjacent to a joint, such that the bone 10 can anchor a suture to repair one or more ligaments or tendons around the bone. In another example, an anchor or suture can help support torn muscles that surround the bone.

The device 100 can be configured to insert an anchor for a suture into a bone of a patient. As shown in FIG. 1, the device 100 can be generally cylindrical, such that the device 100 fits within a hand of a doctor. For example, the device 100 can be designed to fit within the hand of the doctor so that the doctor can operate the device 100 with only one hand. In another example, the device 100 can be designed to be held by a first hand of the doctor and activated or engaged with a second hand of the doctor. In yet another example, the device 100 can be designed to require both hands to be in contact with the device 100 to operate the device 100.

The housing 110 can be configured to protect the device 100 and can be configured to protect components of the device 100 that are within the housing 110. The housing 110 can define a primary shape of the device 100. The housing 110 can include features to improve the ergonomics of the device 100. For example, the housing 110 can include grooves for fingers, palm, or any other portion of a hand. The housing 110 can include an angle such that the device 100 has an ergonomically friendly design. The housing 110 can include a surface texture that helps a doctor hold onto the device 100.

The actuator 112 can be configured to selectively operate the device 100 such that when the doctor engages the actuator 112, the device 100 operates to insert the anchor of the suture into the bone of the patient. The actuator 112 can be a push button, switch, lever, any other device that can be engaged by an operator to communicate with another component of the device 100, or the like. In examples, the actuator 112 can extend from outside the housing 110 to within the housing 110 such that the actuator 112 is engageable with other components, e.g., a servo valve, of the device 100.

The soft tissue anchor receiver 114 can be operable to implant the soft tissue anchor into the bone of the patient. The soft tissue anchor receiver 114 can be removably attached to the device 100. For example, the soft tissue anchor receiver 114 can be threadedly engaged with one or more components of the device 100 to install or remove the soft tissue anchor receiver 114. In examples, the soft tissue anchor receiver 114 can be configured to receive and support a soft tissue anchor before insertion of the soft tissue anchor into the bone of the patient. In an example, at least a portion of the soft tissue anchor receiver 114 can extend outside the housing 110. In another example, the entire body of the soft tissue anchor receiver 114 can be outside the housing 110. The soft tissue anchor receiver 114 can be configured to receive any style, form, or design of anchor that can be used to secure soft tissue to a bone. For example, the soft tissue anchor receiver 114 can be configured to install a JuggerKnot® all suture anchor into the bone of a patient. The device 100 can have multiple versions of the actuator 112 to ensure the versatility of the device 100 and enable the device 100 to work with any number of soft tissue suture anchors. The anchor receiver 114 can have a pointed end to guide the anchor receiver 114 into the bone during the operation of the device 100. For example, anchor receiver 114 can be used to guide the soft tissue anchors into the pre-drilled holes in the bone of the patient such that the soft tissue anchors can be installed without using additional tooling.

Figure 2:
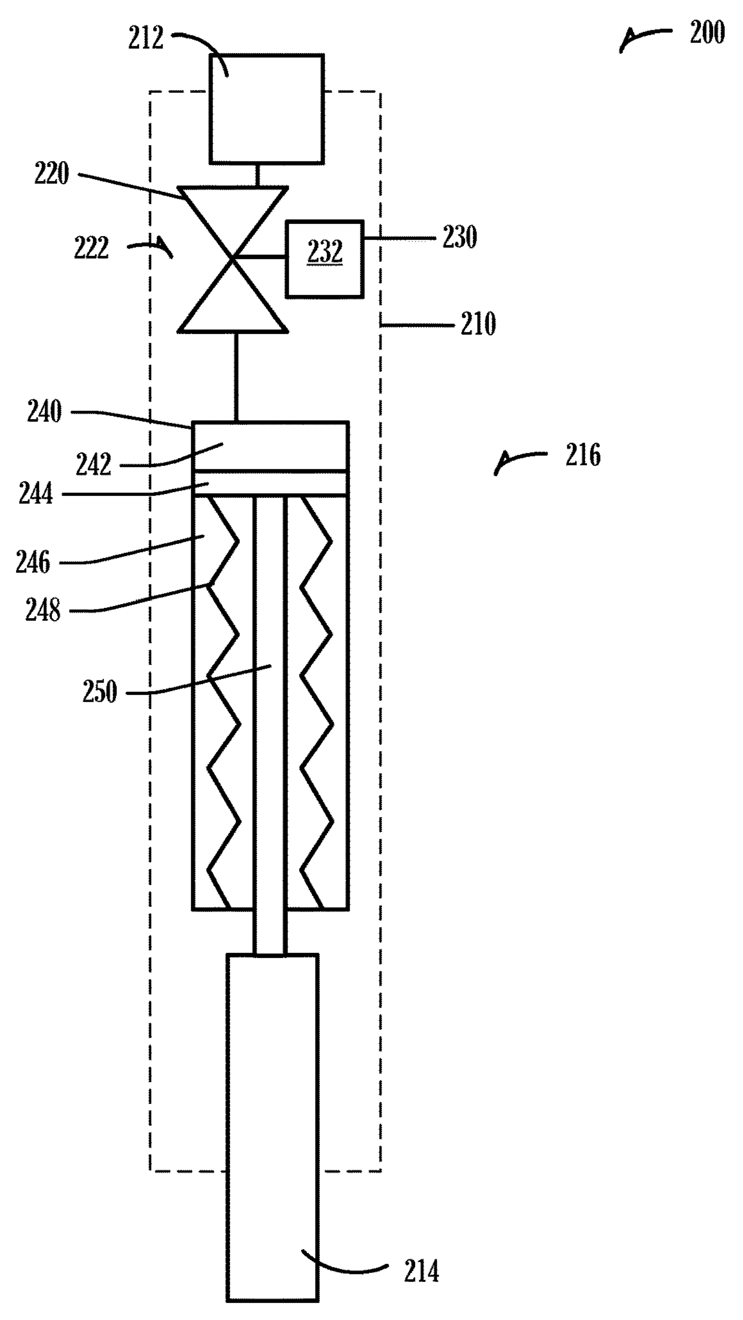
FIG. 2 illustrates a schematic diagram of an example of a handheld self-punching device, according to an embodiment.
Figure 3:
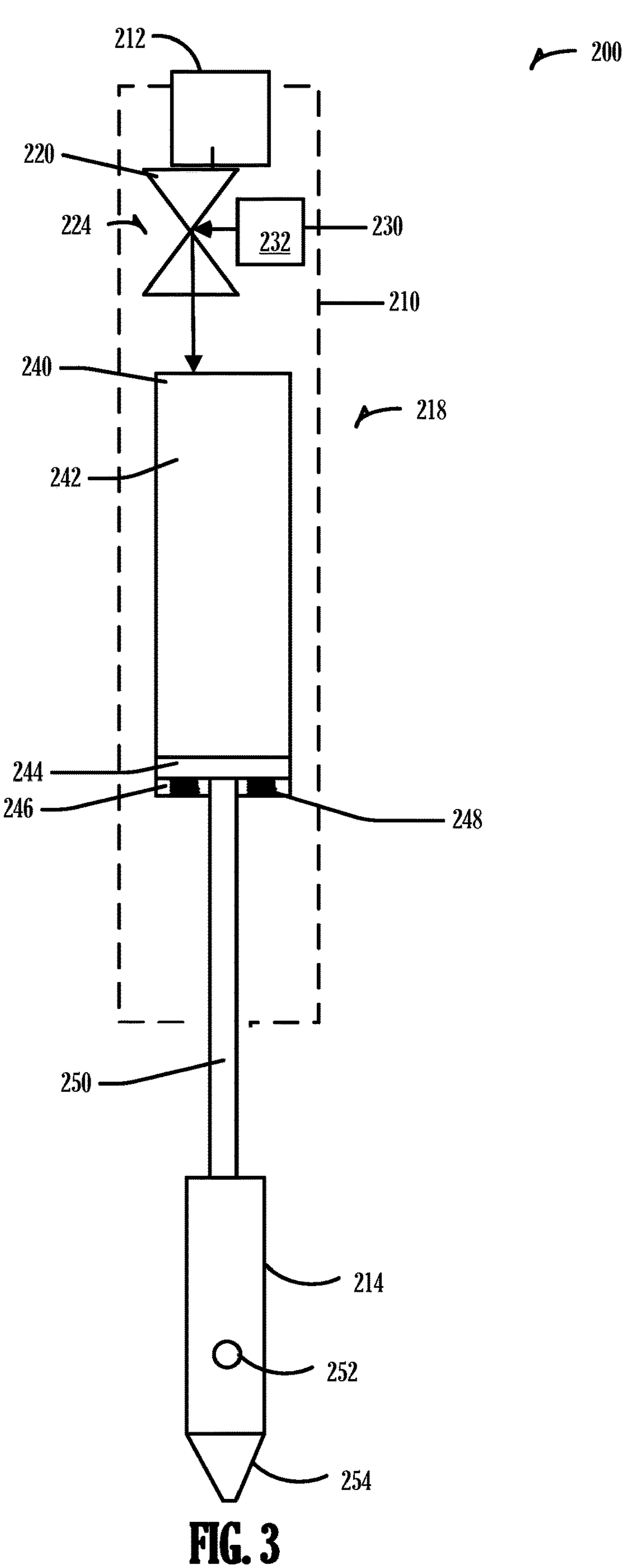
FIG. 3 illustrates a schematic diagram of an example of a handheld self-punching device, according to an embodiment.

FIGS. 2 and 3 will be discussed together. FIG. 2 illustrates a schematic diagram of an example of a handheld self-punching device, e.g., a device 200, according to an embodiment. FIG. 3 illustrates a schematic diagram of an example of the device 200, according to an embodiment. The device 200 can operate between a first position 216, as shown in FIG. 2, and a second position 218, as shown in FIG. 3. The device 200 can include a solenoid valve or a valve 220, an air cartridge or power source 230, and a piston cylinder or a converter 240.

The valve 220 can be configured to selectively fluidically connect the power source 230 and the converter 240. The valve 220 can be installed within the housing 210. In another example, at least a portion of the valve 220 can be outside the housing 210. For example, a portion of the valve 220 that is configured to receive the power source 230 can extend outside of the housing 210. In examples, the valve 220 can be engaged by the actuator 212 to operate the valve 220. In examples, the valve 220 can be operable between a closed position 222 and an open position 224. The valve 220 can be biased to the closed position 222 and moved into the open position 224 when engaged by the actuator 212. The valve 220, and more specifically, the closed position 222 and the open position 224 will be discussed in more detail below.

In an example, the actuator 212 can be an electronic push button that, when compressed, sends an electronic signal to the valve 220 to actuate the valve 220 from the closed position 222 to the open position 224. In another example, the actuator 212 can be a pneumatic push button that, when compressed, fluidically communicates with the valve 220 to actuate the valve 220 from the closed position 222 to the open position 224. In yet another example, the housing 210 can be any form of actuator that can manipulate the valve 220 from the closed position 222 to the open position 224.

The power source 230 can be configured to store power and selectively engage with the converter 240 to activate the converter 240 and implant an anchor of a suture into a bone of the patient. In an example, the power source 230 can be removably inserted into the housing 210 of the device 200. In another example, the power source 230 can be permanently inserted into the housing 210 such that the device 200 can be recyclable or disposable when the power source 230 runs out of stored energy. In another example, the power source 230 can be partially outside the housing 210. When the power source 230 is partially outside the housing 210, the power source 230 can be replaced without opening the housing 210. In such an example, the power source 230 can engage with a quick-connection fitting that is formed into the housing 210 or the valve 220 to enable fast, secure, and reliable replacement of the power source 230.

In examples, the power source 230 can be activated by moving the valve 220 from the closed position 222 to the open position 224. In an example, the power source 230 can be a compressed air cartridge. In such an example, the power source 230 can include compressed air 232 stored within the power source 230. The compressed air 232 can include carbon dioxide. The compressed air 232 can be directed through the valve 220 and to the converter 240 to energize the device 200 and install the suture anchor into the bone of the patient.

The converter 240 can be configured to convert energy from the power source 230 to a mechanical translation to implant the suture anchor into the bone of the patient. In an example, the converter 240 can be installed within the housing 210. In another example, a portion of the converter 240 can be outside the housing 210. In yet another example, the converter 240 can be configured to extend from within the housing 210 to outside of the housing 210.

In an example, the converter 240 can be a piston cylinder. As such, the converter 240 can include a first chamber 242, a piston 244, a second chamber 246, and a piston rod 250. The converter 240 can be selectively fluidically connected to the power source 230 via the valve 220, the piston cylinder can be operable to convert pneumatic or fluidic pressure from the power source 230, e.g., the compressed air 232, to a mechanical translation via a piston rod 250 that can extend outside of the housing 210.

The first chamber 242 can be configured to expand and compress as the converter 240 cycles to transfer power from the power source 230 to a mechanical translation to move the soft tissue anchor receiver 214. Thus, the first chamber 242 can operate between a compressed state and an expanded state. In examples, the first chamber 242 can be connected to the power source 230 when the valve 220 is in the open position 224 and fluidically isolated from the power source 230 when the valve 220 is in the closed position 222. When the valve 220 is in the open position 224, the power source 230 can fill the first chamber 242 with a working fluid, e.g., compressed air, liquid, or the like, to expand the first chamber 242 from the compressed state to the expanded state and move the piston 244 towards the second chamber 246. The first chamber 242 can also include a bleed valve that can open to remove the working fluid from the first chamber 242 after the converter 240 has cycled. Removing the working fluid from the first chamber 242 can help the converter 240 return to equilibrium, e.g., the first chamber 242 can return to the compressed state.

The piston 244 can be within the converter 240. The piston 244 can be positioned between the first chamber 242 and the second chamber 246 such that the piston 244 fluidically isolates the first chamber 242 and the second chamber 246. The piston 244 can be configured to move within the converter 240 to bias toward the first chamber 242 and the second chamber 246. When the valve 220 is in the open position 224, the first chamber 242 can expand, the piston 244 can move toward the second chamber 246 and can extend the piston rod 250 outside the housing 210.

The second chamber 246 can be within the converter 240. The second chamber 246 can be opposite the piston 244 from the first chamber 242. The second chamber 246 can operate between an expanded state and a compressed state such that the piston rod 250 is retracted at least partially within the housing 210 when the second chamber 246 is in the expanded state and the piston rod 250 is extended at least partially outside the housing 210 when the second chamber 246 is in the compressed state. The converter 240 can include springs 248 that are installed within the second chamber 246.

The springs 248 can be installed within the second chamber 246. The springs 248 can engage with an interior surface of the converter 240 to exert a force on the piston 244 and bias the piston 244 toward the first chamber 242. In an example, the device 200 can include a single spring. In yet another example, the device 200 can include any number of the springs 248. The springs 248 can be designed to provide enough force to return the converter 240 back to equilibrium. For example, a length, diameter, or spring stiffness of the springs 248 can be adjusted to alter the force exerted onto the piston 244 by the springs 248. In examples, the springs 248 can be a helical spring, linear spring, shock, damper, or any other device that can be used to exert a force on the piston 244 and bias the piston 244 towards the first chamber 242.

The piston rod 250 can be attached to the piston 244 opposite the first chamber 242 such that the piston rod 250 extends through the second chamber 246. The piston rod 250 can be installed within the housing 210 such that a portion of the piston rod 250 extends outside of the housing 210. In another example, the piston rod 250 can be installed within the housing 210 such that the piston rod 250 is within the housing 210 when the valve 220 is in the closed position 222 and the piston rod 250 extends outside the housing 210 when the valve 220 is in the open position 224. In yet another example, the piston rod 250 can remain within the housing 210 when the valve 220 is in the closed position 222 and the open position 224.

In an example, the converter 240 can have a compression ratio. For example, the compression ratio can be a ratio between a maximum volume of the first chamber 242, e.g., a volume of the first chamber 242 in the expanded state, and a minimum volume of the first chamber 242, e.g., a volume of the first chamber 242 in a compressed state. In examples, the compression ratio can be adjusted to change a force transferred from the converter 240 to the actuator 212 via the piston rod 250. For example, the compression ratio can be greater than 20:1. In another example, the compression ratio can be greater than 15:1. In another example, the compression ratio can be greater than 10:1. In another example, the compression ratio can be greater than 5:1. In another example, the compression ratio can be greater than 2:1. In another example, the compression ratio can be less than 2:1. In an example the compression ratio can range from 2:1 to 20:1. In another example, the compression ratio can range from 1:1 to 10:1. In yet another example, the compression ratio can range from 2:1 to 10:1. In a last example, the compression ratio can be adjusted to ensure that the device 200 generates enough force to insert the suture anchor into the cortico-cancellous region of the bone of the patient.

In an example shown in FIG. 2, the device 200 can be in the first position 216, such that the actuator 212 can be in a non-compressed position such that the actuator 212 does not engage with other components, e.g., the valve 220, of the device 200. In the closed position 222, the valve 220 can isolate the power source 230 and the converter 240. For example, if the power source is air or a liquid, the valve 220 in the closed position 222 can fluidically isolate the power source 230 and the converter 240. In another example, if the power source 230 is electrical, the valve 220 in the closed position 222 can electrically isolate the power source 230 and the converter 240.

In the first position 216, the first chamber 242 can be in the compressed state and the second chamber 246 can be in the expanded state because the piston 244 can be biased toward the first chamber 242. The piston rod 250 can be retracted such that the soft tissue anchor receiver 214 is in a non-extended state.

In the first position 216, the soft tissue anchor receiver 214 can receive the suture anchor in preparation for insertion. The device 200 can also be serviced, for example, to change out the power source 230 when the device 200 is in the first position 216.

As shown in FIG. 3, the device 200 can be in the second position 218, such that the actuator 212 can be in a compressed position and engage with the valve 220. The actuator 212 engages the valve 220 to move the valve 220 from the closed position 222 to the open position 224. In the open position 224, the valve 220 can connect the power source 230 and the converter 240. In open position 224, the valve 220 can connect the power source 230 and the converter 240. For example, if the power source 230 is air or a liquid, the valve 220 in the open position 224 can fluidically connect the power source 230 to the converter 240. In another example, if the power source 230 is electrical, the valve 220 in the open position 224 can electrically connect the power source 230 to the converter 240.

In the second position 218, the first chamber 242 can be in the expanded state and the second chamber 246 can be in the compressed state because the power source 230 can engage with the first chamber 242 to move the piston 244 toward the second chamber 246. The piston rod 250 can be extended such that the soft tissue anchor receiver 214 can be in an extended state. In the second position 218, the soft tissue anchor receiver 214 can hold the suture anchor and provide support to the suture anchor during the installation of the suture anchor into the bone, e.g., the bone 10 (FIG. 1), or the patient. In other words, the soft tissue anchor receive 214 can include a pointed edge such as to guide the suture anchor to install the suture anchor into a pre-drilled hole of the bone without using additional tools.

The device 200 can also be designed such that the device 200 cannot be serviced, e.g., the power source 230 cannot be removed from the device 200, when the device is in the second position 218.

Thus, the soft tissue anchor receiver, e.g., the soft tissue anchor receiver 114 (FIG. 1) or the soft tissue anchor receiver 214, can be operable to implant the soft tissue anchor into a pre-drilled portion of the bone of the patient when the valve 220 is in the open position 224 and the valve 220 fluidically connects the power source 230 (here the power source 230 can include a compressed air) and the converter 240 to fill the converter 240 with compressed air, and the soft tissue anchor receiver 214 extends away from the housing 210 via the piston rod 250.

In examples, the soft tissue anchor receiver 214 can include a threaded surface that is internal to the soft tissue anchor receiver 214 and the piston rod 250 can include an external threaded surface that is complementary to the threaded surface on the soft tissue anchor receiver 214. In another example, the soft tissue anchor receiver 214 and the piston rod 250 can be removably coupled with a pin, socket, or any other removable attachment that can be used to connect the soft tissue anchor receiver 214 and the piston rod 250. The soft tissue anchor receiver 214 can be configured to receive and stabilize a soft tissue anchor during implantation into the bone of a patient.

For example, the soft tissue anchor receiver 214 can include a soft tissue anchor aperture 252 and a pointed end 254. The soft tissue anchor aperture 252 can be configured to receive a soft tissue anchor and hold the soft tissue anchor during the insertion of the soft tissue anchor into the bone of the patient. The pointed end 254 of the soft tissue anchor receiver 214 can guide the soft tissue anchor into the pre-drilled hole when the valve 220 is in the open position 224 and the valve 220 fluidically connects the power source 230 (here the power source 230 can include a compressed air) and the converter 240 to fill the converter 240 with compressed air, and the soft tissue anchor receiver 214 extends away from the housing 210 via the piston rod 250.

Additional Notes & Examples

Example 1 is a device configured to implant a soft tissue anchor into a bone of a patient, the device comprising: a housing; a solenoid valve within the housing, the solenoid valve operable between an open position and a closed position; an air cartridge removably installed at least partially within the housing, the air cartridge including compressed air; a piston cylinder within the housing, the piston cylinder selectively fluidically connected to the air cartridge via the solenoid valve, the piston cylinder operable to convert pneumatic pressure from the compressed air to a mechanical translation via a piston rod that extends outside of the housing; and a soft tissue anchor receiver attached to the piston rod outside of the housing and configured to hold the soft tissue anchor.

In Example 2, the subject matter of Example 1 includes, wherein the soft tissue anchor receiver is operable to implant the soft tissue anchor into the bone of the patient when the solenoid valve is in the open position and fluidically connects the air cartridge and the piston cylinder to fill the piston cylinder with compressed air, and the soft tissue anchor receiver extends away from the housing via the piston rod.

In Example 3, the subject matter of Example 2 includes, wherein in the closed position, the solenoid valve fluidically isolates the air cartridge and the piston cylinder.

In Example 4, the subject matter of Example 3 includes, wherein the piston cylinder comprises: a first chamber fluidically connected to the air cartridge when the solenoid valve is in the open position and fluidically isolated from the air cartridge when the solenoid valve is in the closed position; a piston within the piston cylinder, the piston rod attached to the piston opposite the first chamber; and a second chamber, the piston disposed between the first chamber and the second chamber such that the piston rod extends through the second chamber.

In Example 5, the subject matter of Example 4 includes, wherein the piston cylinder comprises a spring within the second chamber, the spring biasing the piston toward the first chamber.

In Example 6, the subject matter of Examples 4-5 includes, a ten to one compression ratio of a maximum volume of the first chamber to a minimum volume of the first chamber.

In Example 7, the subject matter of Examples 1-6 includes, wherein the device comprises an actuator configured to operate the solenoid valve between the open position and the closed position.

In Example 8, the subject matter of Example 7 includes, wherein the actuator is an electronic push button that, when compressed, sends an electronic signal to the solenoid valve to actuate the solenoid valve from the closed position to the open position.

In Example 9, the subject matter of Examples 7-8 includes, wherein the actuator is a pneumatic push button that, when compressed, fluidically communicates with the solenoid valve to actuate the solenoid valve from the closed position to the open position.

In Example 10, the subject matter of Examples 1-9 includes, wherein the compressed air comprises carbon dioxide.

Example 11 is a device configured to implant a soft tissue anchor into a bone of a patient, the device comprising: a housing; an actuator extending from outside the housing to inside the housing, the actuator engageable by a user to implant the soft tissue anchor, the actuator operable between an open position and a closed position; a power source removably inserted at least partially within the housing, the power source configured to store energy and is controlled by the actuator; a converter within the housing, the converter selectively connected to the power source via the actuator such that in the open position, the actuator connects the converter to the power source to energize the converter, the converter operable to extend a rod outside of the housing; and a soft tissue anchor receiver attached to the rod and configured to hold the soft tissue anchor.

In Example 12, the subject matter of Example 11 includes, wherein the soft tissue anchor receiver operable to implant the soft tissue anchor into the bone of the patient when the actuator is in the open position and connects the power source and the converter to energize the converter, and the soft tissue anchor receiver extends away from the housing via the rod.

In Example 13, the subject matter of Examples 11-12 includes, wherein the power source is a compressed air cartridge within the housing, the compressed air cartridge is configured to store compressed air and is controlled by the actuator.

In Example 14, the subject matter of Example 13 includes, wherein the converter is a piston cylinder, and wherein the actuator, in the open position, fluidically connects the compressed air cartridge and the piston cylinder and the actuator, in the closed position, fluidically isolates the compressed air cartridge and the piston cylinder.

In Example 15, the subject matter of Example 14 includes, wherein the piston cylinder comprises: a first chamber fluidically connected to the compressed air cartridge via the actuator in the open position; a piston within the piston cylinder; a second chamber; and a piston rod attached to the piston opposite the first chamber, wherein the piston is between the first chamber and the second chamber such that the piston rod extends through the second chamber.

In Example 16, the subject matter of Example 15 includes, wherein the piston cylinder comprises a spring within the second chamber, the spring biasing the piston toward the first chamber.

In Example 17, the subject matter of Examples 15-16 includes, a two to one compression ratio of a maximum volume of the first chamber to a minimum volume of the first chamber.

In Example 18, the subject matter of Examples 11-17 includes, wherein the actuator is an electronic push button that when compressed operates from the closed position to the open position.

In Example 19, the subject matter of Examples 11-18 includes, wherein the actuator is a pneumatic push button that when compressed operates from the closed position to the open position.

In Example 20, the subject matter of Examples 11-19 includes, wherein the compressed air comprises carbon dioxide.

Example 21 is an apparatus comprising means to implement of any of Examples 1-20.

Example 22 is a system to implement of any of Examples 1-20.

Example 23 is a method to implement of any of Examples 1-20.

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 10% of the numerical value of the number with which it is being used. Therefore, about 50% means in the range of 45%-55%. Numerical ranges recited herein by endpoints include all numbers and fractions subsumed within that range (e.g., 1 to 5 includes 1, 1.5, 2, 2.75, 3, 3.90, 4, 4.24, and 5). Similarly, numerical ranges recited herein by endpoints include subranges subsumed within that range (e.g., 1 to 5 includes 1-1.5, 1.5-2, 2-2.75, 2.75-3, 3-3.90, 3.90-4, 4-4.24, 4.24-5, 2-5, 3-5, 1-4, and 2-4). It is also to be understood that all numbers and fractions thereof are presumed to be modified by the term "about."

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is to allow the reader to quickly ascertain the nature of the technical disclosure and is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the embodiments should be determined with reference to the appended claims, along with the full scope of equivalents to which such claims are entitled.

The invention claimed is:

1. A device configured to implant a soft tissue anchor into a bone of a patient, the device comprising:

a housing;

an actuator operably coupled to a solenoid valve, at least a portion of the actuator extends outside of the housing, the actuator engageable by a user;

the solenoid valve within the housing, the solenoid valve biased toward a closed position and operable to an open position in response to actuation of the actuator;

an air cartridge removably installed at least partially within the housing, the air cartridge including compressed air;

a piston cylinder within the housing, the piston cylinder comprising:

a first chamber selectively fluidically connected to the air cartridge via the solenoid valve;

a second chamber;

a piston within the piston cylinder and disposed between the first chamber and the second chamber;

a spring within the second chamber, the spring configured to bias the piston toward the first chamber; and a piston rod attached to the piston opposite the first chamber and extending through the second chamber to outside the housing;

wherein the first chamber includes a bleed valve configured to release compressed air from the first chamber after operation of the device to permit the spring to return the piston toward the first chamber; and a soft tissue anchor receiver attached to the piston rod outside of the housing and configured to hold the soft tissue anchor during operation of the device to implant the soft tissue anchor into the bone of the patient;

wherein the piston cylinder is configured to deliver a single pneumatic pulse of sufficient force to drive the soft tissue anchor receiver directly into cortical bone tissue in response to engagement of the actuator.

2. The device of claim 1, wherein the soft tissue anchor receiver is operable to implant the soft tissue anchor into the bone of the patient when the solenoid valve is in the open position and fluidically connects the air cartridge and the first chamber to fill the first chamber with compressed air, and the soft tissue anchor receiver extends away from the housing via the piston rod.

3. The device of claim 2, wherein in the closed position, the solenoid valve fluidically isolates the air cartridge and the first chamber.

4. The device of claim 1, comprising a 10:1 compression ratio of a maximum volume of the first chamber to a minimum volume of the first chamber.

5. The device of claim 1, wherein the actuator comprises an electronic or pneumatic push button.

6. The device of claim 1, wherein the actuator is an electronic push button that, when compressed, sends an electronic signal to the solenoid valve to actuate the solenoid valve from the closed position to the open position.

7. The device of claim 1, wherein the actuator is a pneumatic push button that, when compressed, fluidically communicates with the solenoid valve to actuate the solenoid valve from the closed position to the open position.

8. The device of claim 1, wherein the compressed air comprises carbon dioxide.

9. A device configured to implant a soft tissue anchor into a bone of a patient, the device comprising:

a housing;

an actuator, at least a portion of the actuator extending from outside the housing to inside the housing, the actuator is engageable by a user, the actuator biased toward a closed position and operable to an open position in response to engagement by a user;

a power source removably inserted at least partially within the housing, the power source configured to store energy, the power source selectively connected to a converter via the actuator;

a converter within the housing, the converter comprising:

a first chamber selectively connected to the power source via the actuator when the actuator is in the open position;

a second chamber;

a piston within the converter and disposed between the first chamber and the second chamber;

a biasing element within the second chamber, the biasing element configured to bias the piston toward the first chamber; and a rod coupled to the piston opposite the first chamber and extending through the second chamber and outside of the housing;

wherein the first chamber includes a bleed valve configured to release energy from the first chamber after operation of the device to permit the biasing element to return the piston toward the first chamber; and a soft tissue anchor receiver attached to the rod outside of the housing and configured to hold the soft tissue anchor during operation of the device to implant the soft tissue anchor into the bone of the patient;

wherein the actuator, when engaged by the user, causes the converter to deliver a single pulse of sufficient force to drive the soft tissue anchor receiver and the soft tissue anchor directly into cortical bone tissue in a single forward stroke, and wherein the rod is retracted after delivery of the single pulse while the soft tissue anchor remains implanted in the cortical bone tissue.

10. The device of claim 9, wherein the soft tissue anchor receiver is operable to implant the soft tissue anchor into the bone of the patient when the actuator is in the open position and connects the power source and to the first chamber of the converter, and the soft tissue anchor receiver extends away from the housing via the rod.

11. The device of claim 9, wherein the power source is a compressed air cartridge within the housing, the compressed air cartridge is configured to store compressed air and selectively connectable to the first chamber via the actuator.

12. The device of claim 9, comprising a 2:1 compression ratio of a maximum volume of the first chamber to a minimum volume of the first chamber.

13. The device of claim 9, wherein the actuator is an electronic push button that when compressed operates from the closed position to the open position.

14. The device of claim 9, wherein the actuator is a pneumatic push button that when compressed operates from the closed position to the open position.

15. The device of claim 9, wherein the power source includes compressed air, and wherein the compressed air comprises carbon dioxide.

* * * * *